(12) United States Patent
Levin et al.

(10) Patent No.: US 8,521,280 B2
(45) Date of Patent: *Aug. 27, 2013

(54) METHODS AND APPARATUS TO INCREASE SECRETION OF ENDOGENOUS NATURETIC HORMONES

(75) Inventors: Howard Levin, Teaneck, NJ (US); Mark Gelfand, New York, NY (US)

(73) Assignee: BackBeat Medical, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,068

(22) Filed: Mar. 21, 2012

(65) Prior Publication Data

US 2012/0215272 A1    Aug. 23, 2012

Related U.S. Application Data

(63) Continuation of application No. 11/276,461, filed on Mar. 1, 2006, now Pat. No. 8,165,674.

(60) Provisional application No. 60/657,389, filed on Mar. 2, 2005, provisional application No. 60/678,220, filed on May 6, 2005.

(51) Int. Cl.
*A61N 1/368*    (2006.01)
*A61N 1/36*    (2006.01)

(52) U.S. Cl.
CPC ............ *A61N 1/36117* (2013.01); *A61N 1/368* (2013.01)
USPC ................................................. 607/9; 607/44

(58) Field of Classification Search
USPC ..................................... 607/9, 44
See application file for complete search history.

(56) References Cited

U.S. PATENT DOCUMENTS

| 3,683,934 | A | 8/1972 | Bukowiecki et al. |
|---|---|---|---|
| 3,939,844 | A | 2/1976 | Pequignot |
| 4,712,555 | A | 12/1987 | Thornander et al. |
| 5,213,098 | A | 5/1993 | Bennett et al. |
| 5,601,613 | A | 2/1997 | Florio et al. |
| 5,928,271 | A | 7/1999 | Hess et al. |
| 6,377,852 | B1 | 4/2002 | Bornzin et al. |
| 6,507,756 | B1 | 1/2003 | Heynen et al. |
| 6,668,195 | B2 | 12/2003 | Warman et al. |
| 6,701,187 | B1 | 3/2004 | Bornzin et al. |
| 7,096,064 | B2 | 8/2006 | Deno et al. |
| 7,184,832 | B2 | 2/2007 | Deno et al. |
| 7,233,824 | B2 | 6/2007 | Kleckner et al. |
| 7,286,873 | B2 | 10/2007 | Havel et al. |
| 7,289,849 | B2 | 10/2007 | Baynham |

(Continued)

OTHER PUBLICATIONS

Lopez et al., "Reducing Heart Rate of the Dog by Electrical Stimulation", pp. 414-429, vol. 15 (Circ. Res. 1964).

(Continued)

*Primary Examiner* — Carl H Layno
*Assistant Examiner* — Jessica Sarcione
(74) *Attorney, Agent, or Firm* — Plumsea Law Group, LLC

(57) ABSTRACT

A method and apparatus for treatment of heart failure by increasing secretion of endogenous naturetic hormones ANP and BNP such as by stimulation of the heart atria. Heart pacing is done at an atrial contraction rate that is increased and can be higher than the ventricular contraction rate. Pacing may include mechanical distension of the right atrial appendage. An implantable device is used to periodically cyclically stretch the walls of the appendage with an implanted balloon.

24 Claims, 5 Drawing Sheets

(56) References Cited

U.S. PATENT DOCUMENTS

| | | | |
|---|---|---|---|
| 7,869,874 B2 | 1/2011 | Levin et al. | |
| 8,165,674 B2 * | 4/2012 | Levin et al. | 607/9 |
| 2004/0049235 A1 | 3/2004 | Deno et al. | |
| 2004/0138715 A1 | 7/2004 | Van Groeningen et al. | |
| 2004/0186523 A1 | 9/2004 | Florio | |
| 2005/0038478 A1 | 2/2005 | Klepfer et al. | |
| 2005/0075676 A1 | 4/2005 | Deno et al. | |
| 2005/0090872 A1 | 4/2005 | Deno et al. | |
| 2005/0101998 A1 | 5/2005 | Kleckner et al. | |
| 2006/0173502 A1 | 8/2006 | Baynham | |
| 2007/0299477 A1 | 12/2007 | Kleckner et al. | |
| 2008/0077187 A1 | 3/2008 | Levin et al. | |
| 2010/0094370 A1 | 4/2010 | Levin et al. | |
| 2011/0172731 A1 | 7/2011 | Levin et al. | |

OTHER PUBLICATIONS

Lister et al., "The Hemodynamic Effect of Slowing the Heart Rate by Paired or Coupled Stimulation of the Atria", pp. 362-368 (Am. Heart J. Mar. 1967).

Braunwald et al., "Editorial: Paired Electrical Stimulation of the Heart: A Physiologic Riddle and a Clinical Challenge," pp. 677-681, vol. 32, No. 5 (Circulation Nov. 1965).

Arbel et al., "Successful Treatment of Drug-Resistant Atrial Tachycardia and Intractable Congestive Heart Failure with Permanent Coupled Atrial Pacing," pp. 336-340, vol. 41 (Am. J. or Cardiology Feb. 1978).

"Information Manual, Model 5837 R-Wave Coupled Pulse Generator", 20 pages, Prelim. Ed. III, Medtronic (Jul. 1965).

Siddons et al., Cardiac Pacemakers, pp. 200-217, Pub. No. 680 of American Lecture Series (1968, Charles Thomas Publisher).

Schooderwoerd et al., "Atrial Natriuretic Peptides During Experimental Atrial Tachycardia: Role of Developing Tachycardiomyopathy," pp. 927-932, vol. 15, No. 8 (J. of Cardiovascular Electrophysiology Aug. 2004).

Nishimura, Kazunobu et al., "Atrial pacing stimulates secretion of atrial natriuretic polypeptide without elevation of atrial pressure in awake dogs with experimental complete atrioventricular block." Circ. Res. 1990;66;115-122.

Willems, Rik M.D. et al., "Different Patterns of Angiotensin II and Atrial Natriuretic Peptide Secretion in a Sheep Model of Atrial Fibrillation." Journal of Cardiovascular Electrophysiology. 2001;12. 12;1387-1392.

Zupan, Igor et al., "Effects of Systolic Atrial Function on Plasma Renin Activity and Natriuretic Peptide Secretion after High Rate Atrial and Ventricular Pacing in Dogs." Pace. 2005;28.Supp 1;5270-5274.

Calderone, Angelino "The Therapeutic Effect of Natriuretic Peptides in Heart Failure; Differential Regulation of Endothelial and Inducible Nitric Oxide Syntheses" Heart Failure Reviews, 2003;8;55-70.

Han, Bo et al., "Cardiovascular Effects of Natriuretic Peptides and Their Interrelation with Endothelin-1" Cardiovascular Drugs and Therapy, 2003;17;41-42.

* cited by examiner

Figure 4
Atrial Pacing
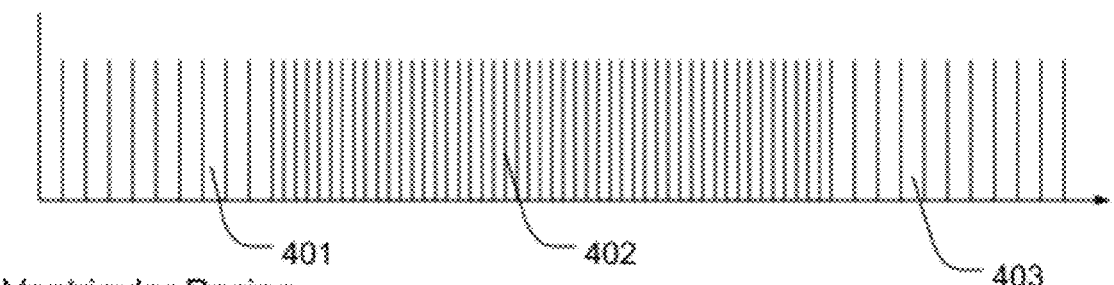
Ventricular Pacing
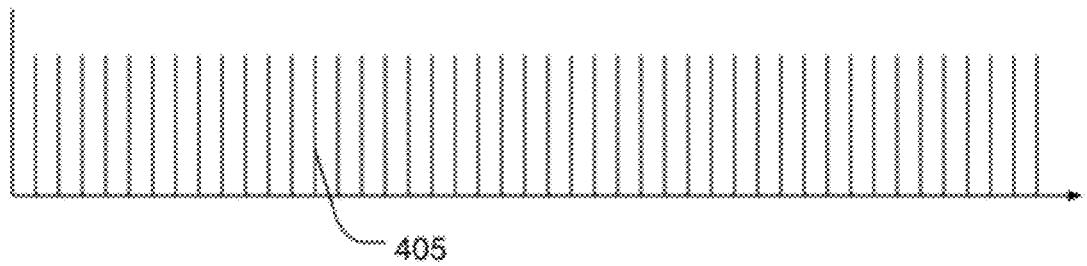

METHODS AND APPARATUS TO INCREASE SECRETION OF ENDOGENOUS NATURETIC HORMONES

This application is a continuation of U.S. application Ser. No. 11/276,461, filed Mar. 1, 2006 (U.S. Patent Publication No. US 2007/0299475, published Dec. 27, 2007), now U.S. Pat. No. 8,165,674, issued Apr. 24, 2012, which claims the benefit of U.S. Provisional Application No. 60/657,389 entitled "Increased Secretion of Endogenous Naturetic Hormones by Atrial Stimulation" filed Mar. 2, 2005 and U.S. Provisional Application No. 60/678,220 having the same title and filed on May 6, 2005, all of which are herein incorporated by reference in their entirety.

BACKGROUND

The present invention generally relates to implantable devices for cardiac stimulation and pacing therapy, and more particularly, the present invention is concerned with cardiac therapies involving the controlled delivery of electrical or mechanical stimulations to the heart for the treatment of congestive heart failure, and an apparatus for delivering such therapies with the objective of altering secretion of hormones by the heart muscle.

Congestive Heart Failure

Congestive heart failure (CHF) occurs when muscle cells in the heart die or no longer function properly, causing the heart to lose its ability to pump enough blood through the body. Heart failure usually develops gradually, over many years, as the heart becomes less and less efficient. It can be mild, scarcely affecting an individual's life, or severe, making even simple activities difficult.

Congestive heart failure (CHF) accounts for over 1 million hospital admissions yearly in the United States (U.S.) and is associated with a 5-year mortality rate of 40%-50%. In the U.S., CHF is currently the most costly cardiovascular disease, with the total estimated direct and indirect costs approaching $56 billion in 1999.

Recent advances in the treatment of CHF with medications, including angiotensin-converting enzyme (ACE) inhibitors, beta-blockers (Carvedilol, Bisoprolol, Metoprolol), Hydralazine with nitrates, and Spironolactone have resulted in significantly improved survival rates. Although many medications have been clinically beneficial, they fall short of clinician's expectations and as a result consideration has turned to procedures and devices as additional and more potent heart failure therapy.

There has been recent enthusiasm for biventricular pacing (pacing both pumping chambers of the heart) in congestive heart failure patients. It is estimated that 30% to 50% of patients with CHF have inter-ventricular conduction defects. These conduction abnormalities lead to a discoordinated contraction of the left and right ventricles of an already failing and inefficient heart. When the right ventricle alone is paced with a pacemaker, the delayed activation of the left ventricle, can also lead to significant dyssynchrony (delay) in left ventricular contraction and relaxation.

Because ventricular arrhythmias continue to threaten CHF patients and many anti-arrhythmic drugs have unacceptable side effects, a sophisticated implantable cardioverter-defibrillator (ICD) device has shown encouraging results. Biventricular pacing in combination with ICDs demonstrates a trend toward improved survival. Preliminary data in animals and humans using subthreshold (of the type that does not by itself cause heart muscle to contract) stimulation of the heart muscle to modulate cardiac contractility are encouraging and may further enhance the quality of life of CHF patients.

It is also clear that many patients with CHF are not candidates for biventricular pacing or do not respond to this treatment strategy. This also applies to other recent advances and experimental therapies. There is a clear need for new, better therapies that will improve and prolong life of heart failure patients and reduce the burden on the medical system. It is particularly important that these new therapies should not require a major surgery, prolonged stay in the hospital or frequent visits to the doctor's office.

Electric Activity of The Heart

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A healthy adult human heart may beat at a rate of 60-80 beats per minute (bpm) while at rest, and may increase its rate to 140-180 bpm when the adult is engaging in strenuous physical exercise, or undergoing other physiologic stress.

The healthy heart controls its rhythm from its sinoatrial (SA) node, located in the upper portion of the right atrium. The SA node generates an electrical impulse at a rate commonly referred to as the "sinus" or "intrinsic" rate. This impulse is delivered to the atrial tissue when the atria are to contract and, after a suitable delay (on the order of 140-220 milliseconds), propagates to the ventricular tissue when the ventricles are to contract. SA node is the natural pacemaker of the heart. If it is disabled, there are other specialized areas of the heart muscle that can generate an intrinsic heart rate.

The ventricular muscle tissue is much more massive than the atrial muscle tissue. The atrial muscle tissue need only produce a contraction sufficient to move the blood a very short distance from the respective atrium to its corresponding ventricle. The ventricular muscle tissue, on the other hand, must produce a contraction sufficient to push the blood through the complete circulatory system of the entire body. Even though total loss of atrial contraction can lead to a small reduction of cardiac output it is not an immediate risk to life.

Electronic Cardiac Pacemakers

It is the function of a electronic pacemaker (pacemaker) to provide electrical stimulation pulses to the appropriate chamber(s) of the heart (atrium, ventricle, or both) in the event the heart is unable to beat on its own (i.e., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the "escape interval"), then a stimulation pulse is generated at the conclusion of this prescribed period of time and delivered to the appropriate heart chamber via a pacemaker lead. Pacemaker leads are isolated wires equipped with sensing and stimulating electrodes.

Modern programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

Much has been written and described about the various types of pacemakers and the advantages and disadvantages of each. For example, U.S. Pat. Nos. 4,712,555 of Thornander et al. and 5,601,613 of Florio et al. present background information about pacemakers and the manner in which they interface with a patient's heart. These patents are hereby incorporated by reference in their entirety.

One of the most versatile programmable pacemakers available today is the DDDR pacemaker. This pacemaker represents a fully automatic pacemaker which is capable of sensing and pacing in both the atrium and the ventricle, and is also capable of adjusting the pacing rate based on one or more physiological factors, such as the patient's activity level. It is commonly accepted that the DDDR pacemaker is superior in that it can maintain AV synchrony while providing bradycardia (slow hear beat) support. It is also generally more expensive than other, simpler types of pacemakers. A description of DDDR pacing is included in this discloser as a state of the art.

In general, DDDR pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR).

It is accepted as important and advantageous, for the patient with complete or partial heart block, that the PV state of the DDDR pacemaker tracks the atrial rate, which is set by the heart's SA node, and then paces in the ventricle at a rate that follows this atrial rate. It is advertised that because the rate set by the SA node represents the rate at which the heart should beat in order to meet the physiologic demands of the body (at least for a heart having a properly functioning SA node) the rate maintained in the ventricle by such a pacemaker is truly physiologic.

In some instances, a given patient may develop dangerously fast atrial rhythms, which result from a pathologic arrhythmia such as a pathological tachycardia, fibrillation or flutter. In these cases, a DDDR pacemaker may pace the ventricle in response to the sensed atrial arrhythmia up to a programmed maximum tracking rate (MTR). The MTR defines the upper limit for the ventricular rate when the pacemaker is tracking the intrinsic atrial rate. As a result, the MTR sets the limit above which the ventricles cannot be paced, regardless of the intrinsic atrial rate. Thus, the purpose of the MTR is to prevent rapid ventricular stimulation, which could occur if the intrinsic atrial rate becomes very high and the pacemaker attempts to track atrial activity with 1:1 AV synchrony.

When the intrinsic atrial rate exceeds the MTR the pacemaker may initiate one or more upper atrial rate response functions—such as automatically switching the pacemaker's mode of operation from an atrial tracking mode to a non-atrial rate tracking mode.

The heart's natural response to a very high atrial rate involves a natural phenomenon known as "blocking"—where the AV node attempts to maintain a form of AV synchrony by "dropping out" occasional ventricular beats when the high atrial rate exceeds a certain natural threshold i.e., the refractory period of the heart tissue. The blocking phenomenon is often expressed as a ratio of the atrial beats to the ventricular beats (e.g. 6:5, 4:3, etc.). Of particular importance is a 2:1 block condition where there are two atrial beats for every one ventricular beat. The 2:1 block condition is a natural response to a very high atrial rate, during which full ventricular rate synchronization (i.e. at a 1:1 ratio) would be dangerous to the patient.

Some known pacemakers emulate this 2:1 condition, by tracking P-waves up to the device's programmed total refractory period (TARP) of the heart. That is, P-waves which fall in the total refractory period are not tracked, and the device is said to have a "2:1 response mode". During the 2:1 block response mode, the ventricles are paced at a lower rate than the natural atrial rate, because P-waves occurring soon after ventricular events are ignored for the purposes of calculating the ventricular pacing rate. As a result, the 2:1 block response mode prevents the pacemaker from pacing the ventricles at a tachycardia rate.

The 2:1 block response mode is an effective response for dealing with short incidences of high atrial rates and in preventing occurrence of a pacemaker mediated tachycardia resulting from retrograde P-waves. However, the 2:1 block response mode may become uncomfortable for the patient if it is maintained for an extended period of time due to programmed long atrial refractory periods, because the pacing rate will be ½ of the required physiologic rate.

Many more advanced pacemaker operation modes have been described and sometimes implemented. Some of these modes included sensing abnormally high atrial rates and prevented them from causing rapid ventricular rates. Common to prior pacing no attempt has been made to induce a rapid (faster than normal) atrial rate by pacing or to pace atria at rate higher than ventricles.

Natriuretic Peptides (ANP and BNP)

Atrial natriuretic peptide (ANP) is a hormone that is released from myocardial cells in the atria and in some cases the ventricles in response to volume expansion and increased wall stress. Brain natriuretic peptide (BNP) is a natriuretic hormone that is similar to ANP. It was initially identified in the brain but is also present in the heart, particularly the ventricles.

The release of both ANP and BNP is increased in heart failure (CHF), as ventricular cells are recruited to secrete both ANP and BNP in response to the high ventricular filling pressures. The plasma concentrations of both hormones are increased in patients with asymptomatic and symptomatic left ventricular dysfunction, permitting their use in diagnosis. A Johnson and Johnson Company Scios sells popular intravenous (IV) medication Natrecor (nesiritide), a recombinant form of the endogenous human peptide for the treatment of decompensated CHF. The advent of Natrecor marked an important evolution in the understanding and treatment of acute heart failure.

Both ANP and BNP have diuretic, natriuretic, and hypotensive effects. They also inhibit the renin-angiotensin system, endothelin secretion, and systemic and renal sympathetic activity. Among patients with CHF, increased secretion of ANP and BNP may partially counteract the effects of norepinephrine, endothelin, and angiotensin II, limiting the degree of vasoconstriction and sodium retention. BNP may also protect against collagen accumulation and the pathologic remodeling that contributes to progressive CHF.

SUMMARY

Increasing levels of ANP and/or BNP in blood would benefit heart failure patients. Unfortunately ANP and BNP cannot be taken as an oral medication since it is a peptide and will be destroyed in the patient's digestive system. BNP is currently available as an IV injectable medication. This limits its use to hospitals and special therapy centers. Many patients would benefit from the increased blood levels of ANP and BNP if the therapy did not require such professional settings and was a part of their normal life.

There is a desire to cause a therapeutic increase of blood plasma ANP and BNP via an increased endogenous release of ANP and BNP from the atria of the patient's heart. Atrial release is mediated via increase of atrial wall stress. The embodiments disclosed here include among others: the mechanical distension of the atria or atrial appendage, rapid pacing of the atria or subthreshold electric stimulation of atria.

Increased heart rates, seen with supraventricular tachycardia (SVT), are clinically associated with polyuria, or increased urine output. The start of the polyuria is coincident with the start of the tachycardia and finishes with the end of the rapid rate. This observation was confirmed in humans by pacing them at high rates, which caused an increase in ANP secretion within the first 30 minutes of pacing.

Electric Stimulation of the Heart

One embodiment disclosed here uses a modified implanted electronic cardiac pacemaker to increase ANP and BNP secretion by pacing the right atrium of the patient at an appropriately high rate. At the same time it generally is not desired to substantially increase the ventricular contraction rate of HF patients. Ventricular ejection at a rate substantially above normal may result in the insufficient time for the heart to relax and to refill with blood between the contractions.

Current cardiac pacemakers with the capability of pacing both the atrium and the ventricle stimulate the heart chambers in a "1:1" ratio, that is no more than one ventricular stimulus per atrial stimulus and vice versa. Few normal people, and certainly no patient with CHF, can tolerate high ventricular rates without hemodynamic compromise from decreased filling. This is one of the reasons many previous therapies have chosen to try to slow heart rate in CHF and why beta-blockers or other negative chrontropic agents (drugs that slow down the heart rate) are preferred in the clinical treatment of CHF. For the purpose of this invention it would be desirable to have a device where the atrium could be stimulated at a high rate to cause release of ANP/BNP but without causing clinically unacceptably high ventricular rates. For example, atrial rates could range from 120 to 240 bpm with ventricular rates in the range of 50 to 110 per minute during pacing intended to release endogenous ANP/BNP. These rates would return to the normal ranges and atrial:ventricular stimulation ratio (i.e., 1:1) pacing as is in currently clinically available pacemakers when the therapy is interrupted or stopped.

In the described embodiment patients have either a natural atrioventricular block (AV block) or have an AV block induced by heart tissue ablation or some other appropriate procedure. For example in patients with a so-called third-degree AV block (complete AV block, no AV conduction), no atrial impulses reach the ventricles, and ventricular rhythm is maintained by a subsidiary natural pacemaker. Since subsidiary pacemakers must be below the level of block, their location is in part determined by the site of block. In third-degree AV nodal block, the ventricular rhythm is usually maintained by pacemakers in the AV junction with resultant narrow QRS complexes. In third-degree AV block localized to the bundle branches, ventricular rhythm is maintained by a pacemaker in the Purkinje fibers, with resultant wide QRS complexes. The junctional pacemaker rate is usually faster (40-80 beats/min) compared with the peripheral Purkinje network (20-40 beats/min). In such patients a dual chamber pacemaker can be used to pace atria at a rate much higher than the ventricles without the risk of patient developing dangerous ventricular tachycardia (rapid heart beat). An atrioventricular (AV) node ablation is a known medical procedure that destroys a part of the heart's normal electrical system. The combination of pacing and AV node ablation is sometimes used clinically in patients with chronic atrial fibrillation and rapid ventricular response that poorly respond to drug therapy.

This is accomplished by cauterizing the AV node, which is located between the upper heart chamber (atria) and the lower heart chambers (ventricles). Once the AV node is cauterized, none or few impulses from the atria will be able to reach the ventricles. Currently an AV node ablation is performed when the patient's rhythm disturbance (arrhythmia) originates in the atria and cannot be controlled adequately. A permanent pacemaker is installed afterwards, to keep the heart beating at a normal pace. The pacemaker lead is connected directly to a ventricle.

Electronic pacemakers are currently used to replace or supplement the natural pacing nodes of the heart by applying electric excitory signals to the heart muscle to cause contraction and blood pumping cycle. Pacemakers are used in patients with diseased nodes (slow heart beat) and defective (blocked) conduction pathways. Bi-ventricular pacemakers pace both ventricles of the heart to restore synchrony between the ventricles.

Generally, the conventional wisdom of all pacing therapies for the heart disease is as follows. A human heart consists of four chambers—two atria and two ventricles. In order for the heart to efficiently perform its function as a pump, the atrial muscles and ventricular muscles should contract in a proper sequence and in a timed relationship, as they do in a healthy heart. Therefore electronic pacemakers are used to restore the normal heartbeat or to restore synchrony between different chambers of the heart.

The inventors broke away from this tradition and proposed a counterintuitive approach to heart pacing. In the invention a pacemaker is counter intuitively used dissynchronously to generate different atrial and ventricular contraction rates. Specifically a higher rate of atrial contractions than ventricular contractions is generated. It is understood that this may result in suboptimal performance of the heart. Inventors propose that this disadvantage will be offset by the benefit of the increased ANP-BNP secretion by the heart atria in heart failure patients.

Mechanical Stimulation

There is a desire to cause a therapeutic increase of blood plasma ANP and BNP via an increased endogenous release of ANP and BNP from the atria of the patient's heart. Atrial release is mediated via increase of atrial wall stress. The embodiments disclosed herein include among others: the mechanical distension of the atria or atrial appendage, rapid pacing of the atria or subthreshold electric stimulation of atria.

One embodiment uses an implantable expandable device (such as an inflatable balloon) placed in an atrial appendage of the heart to cause a therapeutic increase of blood plasma ANP and BNP via an increased endogenous release of ANP and BNP in response to the artificially induced changes of the atrial wall stress. The wall stress is caused by periodic inflation of the balloon to the size that exceeds normal size of the appendage therefore distending its walls.

It is know in the field of cardiology that stretching or otherwise stressing tissue in the walls of the atria of the heart initiates the release of endogenous ANP-BNP. No practical therapy or medical device resulted from this knowledge for the lack of a safe and simple method and a technology enabling such release repeatedly over clinically relevant duration of time.

The right atrial appendage (RAA) or the right auricle of the heart is the appendicular portion of the right atrium that externally originates from the terminal groove. In man, the RAA has a characteristic triangular "pocket" shape and resides inside the pericardial sac on top of the anterior (frontal) surface of the heart. The right atrial appendage is lined internally by pectinate muscles that originate from the terminal crest. The function of the RAA is unclear and its removal or isolation by surgery is not known or expected to have to have serious adverse effects on the patient.

An implantable or implanted device (commonly termed an "implant") is an artificial device fully enclosed in the patient's body. It is significant that implants allow the natural skin of the patient to serve as a barrier against infection. Relevant to this invention an implant can include, for example, an inflatable balloon, a complex electromechanical pump, a catheter and/or an infusion port. Implantation can be achieved by open surgery, minimally invasive surgery or a transcatheter intervention, whether extravascular, intravascular or combination of any of the above. During the implantation procedure, a surgical instrument or catheter is used to cross the skin, penetrating into the patient's body. The implant is positioned at the desired site and the pathway used to access the site is closed. The site heals and the device is now fully implanted.

Cyclically stretching or otherwise stressing the atria of a patient can result in benefits other or in addition to simple ANP and BNP release. Such benefits can include activation of neuron-hormonal mechanisms and additional release of other hormones that can benefit patients with high blood pressure and heart failure. Of particular importance for the invention are known physiologic pathways between the heart muscle, the brain and the kidneys that can result in vasodilatation of blood vessels and increased urine output in response to atrial stretch. Full description of these interactions goes beyond the scope of this invention and can be obtained from literature on cardio-renal physiology.

Stretching or otherwise stressing the atria of a patient can be achieved in many different ways, for example, by pulling on the atrial appendage, pulling on the atria or on the junctions between the great vessels and the heart atria.

The choice of an inflatable balloon implanted in the right atrial appendage was justified by its simplicity but other controllably expandable medical devices could potentially serve the same purpose.

The right atrial appendage is not the only part of the heart that, when stressed by stimulation, can release beneficial hormones. The choice of the site was justified by the easy surgical and vascular access and low risk of blood clotting. It is understood that similar manipulation of, for example, left atrial appendage, can achieve similar results.

SUMMARY OF THE DRAWINGS

A preferred embodiment and best mode of the invention is illustrated in the attached drawings that are described as follows:

FIG. 4 illustrates intermittent asynchronous pacing.

DETAILED DESCRIPTION

Figure 1:
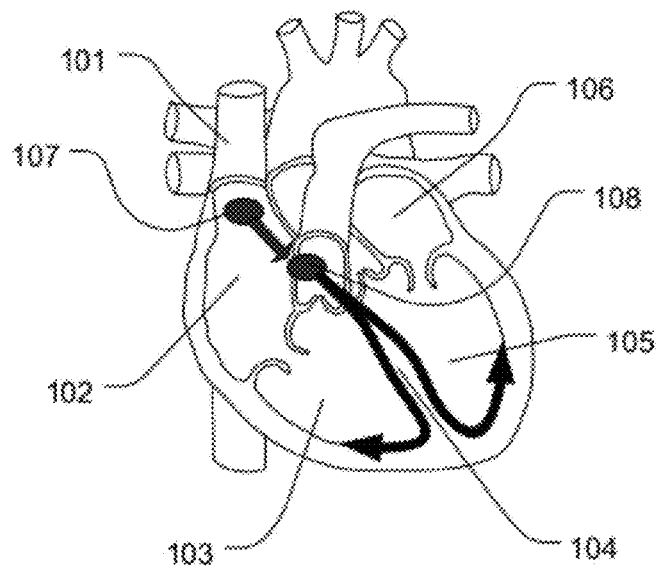
FIG. 1 illustrates the electric excitory pathways and chambers of a human heart.

FIG. 1 shows a normal heart. Electrical pulses in the heart are controlled by special groups of cells called nodes. The rhythm of the heart is normally determined by a pacemaker site called the sinoatrial (SA) node 107 located in the posterior wall of the right atrium 102 near the superior vena cava (SVC) 101. The SA node consists of specialized cells that undergo spontaneous generation of action potentials at a rate of 100-110 action potentials ("beats") per minute. This intrinsic rhythm is strongly influenced by autonomic nerves, with the vagus nerve being dominant over sympathetic influences at rest. This "vagal tone" brings the resting heart rate down to 60-80 beats/minute in a healthy person. Sinus rates below this range are termed sinus bradycardia and sinus rates above this range are termed sinus tachycardia.

The sinus rhythm normally controls both atrial and ventricular rhythm. Action potentials generated by the SA 107 node spread throughout the atria, depolarizing this tissue and causing right atrial 102 and left atrial 106 contraction. The impulse then travels into the ventricles via the atrioventricular node (AV node) 108. Specialized conduction pathways that follow the ventricular septum 104 within the ventricles rapidly conduct the wave of depolarization throughout the right 103 and left 105 ventricles to elicit the ventricular contraction. Therefore, normal cardiac rhythm is controlled by the pacemaker activity of the SA node and the delay in the AV node. Abnormal cardiac rhythms may occur when the SA node fails to function normally, when other pacemaker sites (e.g., ectopic pacemakers) trigger depolarization, or when normal conduction pathways are not followed.

Figure 2:
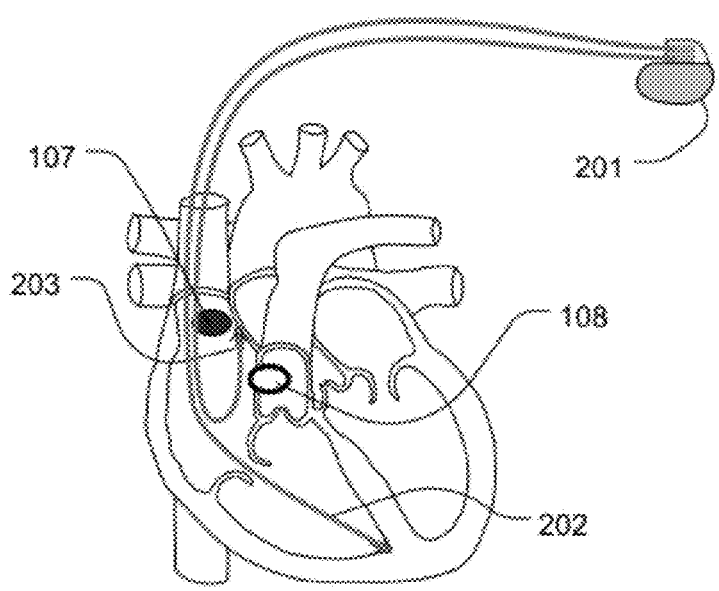
FIG. 2 illustrates the embodiment of the invention with a two lead pacing system.

FIG. 2 shows a heart treated with one embodiment of the invention. Pulse generator (pacemaker) 201 is implanted in a tissue pocket in the patient's chest under the skin. In this embodiment the generator 201 is connected to the heart muscle by two electrode leads. The ventricular lead 202 is in contact with the excitable heart tissue of the right ventricle 103. The atrial lead 203 is in contact with the excitable heart tissue of the right atrium 102. It is understood that the pacemaker can have more leads such as a third lead to pace the left ventricle 105. It is expected that in future cardiac pacemakers will have even more leads connecting them to various parts of the anatomy.

Leads 203 and 202 can combine sensing and pacing electrodes as known and common in the field. The atrial lead 203 can therefore sense the natural intrinsic contractions of the atria before they occur and communicate them to the generator 201. The generator is equipped with the programmable logic that enables it to sense signals, process the information, execute algorithms and send out electric signals to the leads.

In this embodiment the natural conduction path between the SA node 107 and the AV node 108 is blocked. The patient may already have a natural complete AV block. In this case no intervention is needed. If the patient has functional electric pathways from atria to ventricles, the patient's AV node can be disabled (blocked) by tissue ablation. It is understood that many irreversible and reversible methods of selectively blocking conduction in the heart are known. These include treatment with chemical agents and blocking with subthreshold electric stimulation (non-excitatory stimulation that does not cause muscle fibers to contract). Ablation of the AV node is used as an example since it is widely accepted and easily performed using RF energy catheters. Other devices that use cold, laser and ultrasound energy to perform ablation are also known.

Figure 3:
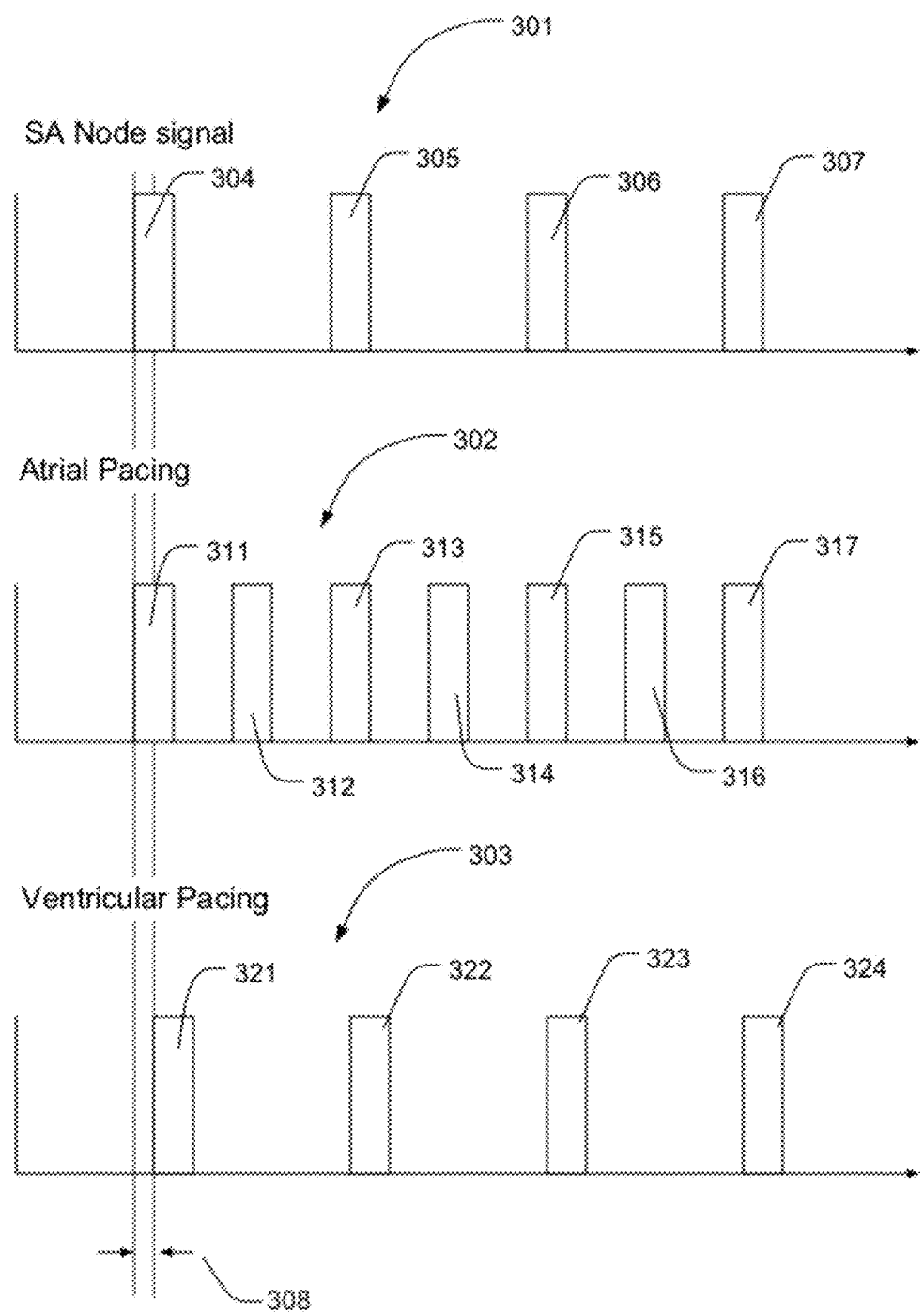
FIG. 3 illustrates one sequence of natural and induced stimulation pulses.

FIG. 3 illustrates one possible embodiment of the invention with a sequence of stimulation pulses. Pulses are simplified and presented as rectangular blocks spaced in time as represented by the X-axis.

Trace 301 illustrates the natural or intrinsic rate generated by the SA node of the heart. The SA node generates pulses 304, 305, 306 and 307. These pulses can be sensed by the atrial lead 203.

In response to the sensing of intrinsic atrial pulses, the pulse generator 201 generates a series of pulses represented by the trace 302. Pulses are conducted to the atria by the atrial lead 203. Device generated atrial stimulation pulses 311, 313, 315 and 317 are in synchrony with the SA node pulses 304, 305, 306 and 307. They represent the intrinsic heart rate. The generator 201 (based on an embedded algorithm) also generates extra atrial pulses 312, 314 and 316. Together synchronous pulses 311, 313, 315, 317 and asynchronous pulses 312, 314, 316 determine the atrial rate of the heart.

Trace 303 represents ventricular stimulation pulses 321, 322, 323 and 324 conducted to the ventricle of the heart by the ventricular lead 202. The AV node of the heart in this embodiment is blocked. Therefore the ventricular stimulation is generated by the generator 201 based on an embedded algorithm. To ensure better performance of the heart ventricular pulses 321, 322, 323 and 324 are synchronized to the synchronous atrial pulses 311, 313, 315 and 317 with a short delay 308 determined by the embedded algorithm that simulates the natural delay of the AV node conduction.

The algorithm illustrated by the FIG. 3 can be described as a following sequence:
  a. sensing an intrinsic SA node pulse (P-wave),
  b. generating a synchronous atrial pacing pulse,
  c. calculating the intrinsic atrial rate based on previous SA node pulse intervals,
  d. generating synchronous ventricular pacing signal delayed from the synchronous atrial pacing signal at the ventricular rate equal to the intrinsic SA node excitation rate (sinus rhythm),
  e. calculating the desired increased atrial rate, such as for example, a 2:1 (A:V) rate,
  f. generating asynchronous atrial pacing signal based on the calculated increased atrial rate, and
  g. waiting for the next intrinsic SA node pulse (P-wave).

It is understood that this example of an algorithm is an illustration and many other embodiments of the invention can be proposed. It can be envisioned that more than 2:1 (atrial: ventricular) rate can be tolerated by the patient or that less than 2:1 rate is desired such as accelerating every second atrial beat.

It may be not essential to preserve the natural sinus rhythm (from the SA node) is preserved. In some patients it may be desired for the algorithm to take over the heart rate and force all the atrial contraction. Pacing modalities that do not rely on the SA node to generate the heart rate are known and used to treat bradycardia. The SA node of a patient can be ablated similar to the AV node and the embedded pacemaker algorithm will pace the atria. Alternatively, atria may be paced if the natural SA node pulse is not senses within the expected time from the last ventricular contraction. Various activity sensors such as accelerometers can be used to accelerate the heart rate as needed.

FIG. 4 illustrates intermittent application of the proposed therapy. It is possible that some patients will not need or will not be able to tolerate continuous asynchronous A-V (atria-ventricular) pacing. In such patient period of normal (synchronous) pacing 401 is followed by the period of asynchronous (accelerated atrial) pacing 402 followed again by the period of synchronous pacing 403. The ventricular pacing rate 405 in this example stays the same. Switching between rates can be based on timing, patient's activity or physiologic feedbacks. For example, the pattern of therapy using electrical stimuli to generate high atrial rates can be intermittent of varying duration of accelerated atrial pacing in intervals of 10-60 minute durations occurring, for example, 3 times per day.

Commonly, in comparison to previous devices, this embodiment of the invention purposefully creates ratios of atrial to ventricular contraction higher than 1:1, such as for example in the range of 1:1 to 4:1. In addition, any previous device that allowed more that a 1:1 ratio of contraction based this relationship on sensing native atrial depolarization and deferring generation of a ventricular pacing stimulus (skipping premature ventricular beats). In contrast, in the illustrated embodiment, the higher than 1:1 rate is intentionally and controllably initiated by the implantable generator. As a result the atrial rate is increased to a rate which causes the release of sufficient endogenous naturetic hormone to result in a therapeutically beneficial increase in blood plasma levels of the hormones or increased levels in any other vascular or non-vascular space in which these hormones a found.

It is desirable to cause a therapeutic increase of blood plasma ANP and BNP via an increased endogenous release of ANP and BNP from the atria of the patient's heart. Atrial release is mediated via increase of atrial wall stress. The best embodiment of the invention known to the inventors at the time of the invention is rapid pacing of the atria that is expected to increase the rate of contractions of the atria and release ANP and BNP. The invention has been described in connection with the best mode now known to the applicant inventors. The invention is not to be limited to the disclosed embodiment. Rather, the invention covers all of various modifications and equivalent arrangements included within the spirit and scope of the appended claims.

FIG. 1 shows a normal heart. Electrical pulses in the heart are controlled by special groups of cells called nodes. The rhythm of the heart is normally determined by a pacemaker site called the sinoatrial (SA) node 107 located in the posterior wall of the right atrium 102 near the superior vena cava (SVC) 101. The SA node consists of specialized cells that undergo spontaneous generation of action potentials at a rate of 100-110 action potentials ("beats") per minute. This intrinsic rhythm is strongly influenced by autonomic nerves, with the vagus nerve being dominant over sympathetic influences at rest. This "vagal tone" brings the resting heart rate down to 60-80 beats/minute in a healthy person. Sinus rates below this range are termed sinus bradycardia and sinus rates above this range are termed sinus tachycardia.

Figure 5:
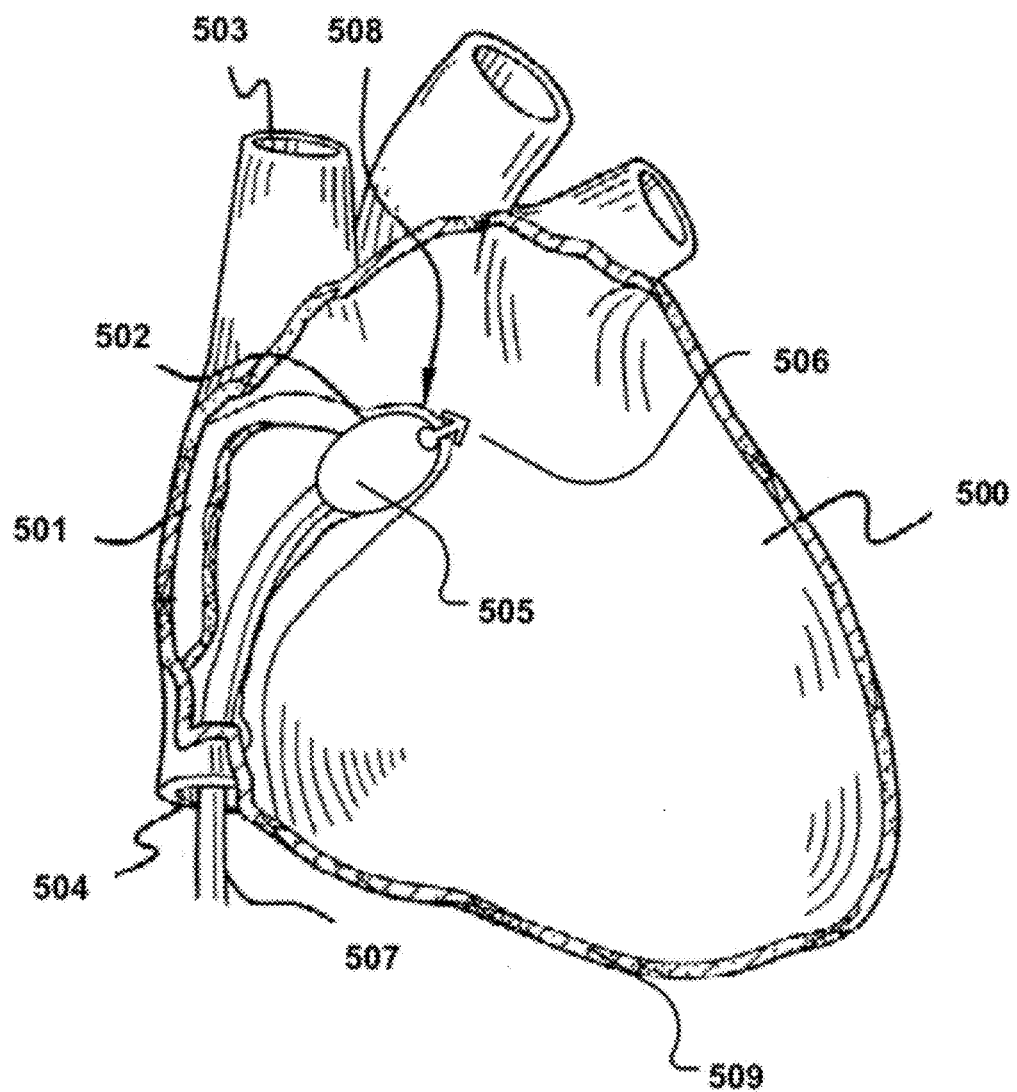
FIG. 5 illustrates an inflatable balloon in right atrial appendage of the heart.

FIG. 5 shows a human heart 500 treated with one embodiment of the invention. Heart is shown inside the pericardial sac 509 that is cut open. Heart has a right atrium (RA) 501, a superior vena cava (SVC) 503 and an inferior vena cava (IVC) 504. The purpose of the embodiment is to stretch the walls of the right atrial appendage (RAA) 502. The RAA stretching results in the ANP and BNP increase and benefits to patients with heart disease and such as heart failure (CHF) or hypertension. RAA stretching is achieved by periodically expanding the inflatable balloon 505 inside the RAA. The balloon 505 is mounted on the tip of the catheter 507. The catheter 507 is connected with an inflation device (See FIG. 2) that can be implanted elsewhere in the body. Both IVC 504 and SVC 503 can be used to advance the catheter into the RA 501 and further into RAA 502. Methods of placing and securing similar devices in the RA of the heart are well known in the field of electrophysiology and cardiology and routinely used to place pacemaker electrode leads in patients. In the illustrated embodiment the balloon 505 is advanced deep into the apex 508 of the RAA 502 and secured there with an anchor 506. The purpose of advancing the balloon into the apex and securing it there is to reduce the probability of clotting of the blood in the stagnant blood flow zones formed by the balloon and to prevent the balloon from floating out or the RAA. The anchor 506 can be a barb or a screw similar to ones used to anchor pacemaker leads in the heart. The surface of the balloon can be made of a material or is externally coated with a material such as porous ePTFE that encourages in-growth of tissue. It is known that, when a tissue implant is porous with pore entry diameters larger than approximately 20 to 500 microns, tissue grows into these pores. This phenomenon appears desirable in many medical device applications because it makes an implant one with the implanted organ and in theory it allows tissue ingrowth into the implant and reduces capsular contraction. This way in several weeks after the implantation the balloon 505 will be fused with the inner walls of the RAA 502 to further prevent clotting or dislodgement of the balloon.

Figure 6:
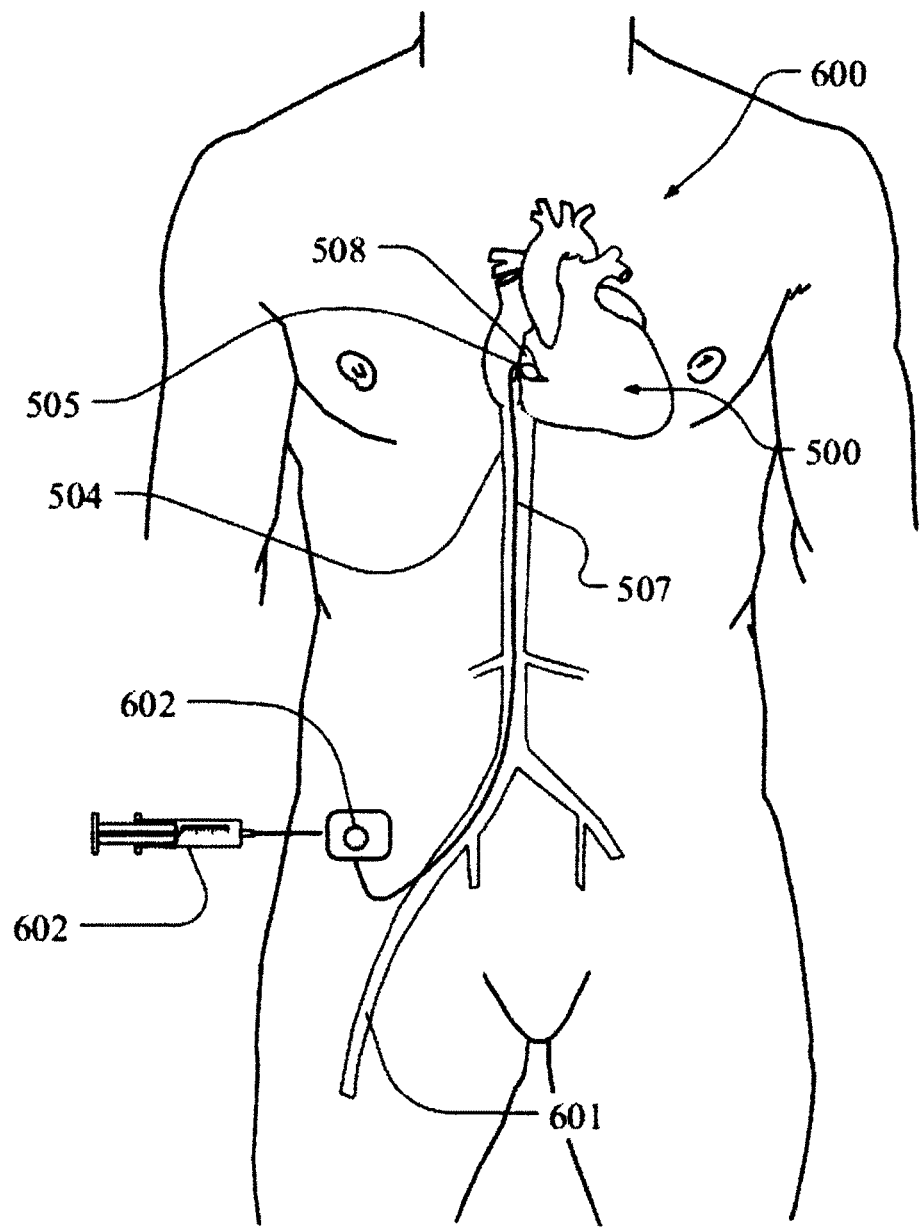
FIG. 6 illustrates the embodiment of the invention with a two lead pacing system.

FIG. 6 shows a patient 600 treated with one embodiment of the invention. Fluid pump 602 is implanted in a tissue pocket in the patient's body under the skin. In this embodiment the pump 602 is connected to the balloon 505 placed in the RAA 508 by the fluid filled catheter 507. It is understood that the pump 602 can be implanted elsewhere in the body, that the catheter 507 can follow a different vascular route and that the balloon 505 can be placed in different locations in the RA or Left Atrium (LA) of the heart. These modifications to the embodiment will not change the substance of the invention.

An implantable pump 602 is an implantable device that is inserted under the patient's skin and can be refilled using a transdermal needle 602 access. An implantable pump may be attached to a separate catheter 507 that delivers fluid to and from the expandable balloon 505. Depending on the desired treatment modality, a preferred implantable pump can be programmable, patient controlled or physician controlled. The pump can be mechanical (activated by finger pressure) or electro-mechanical using motors or solenoid pistons to generate flow and pressure.

The catheter 504 can be introduced into the RAA space under fluoroscopic, MRI or CT guidance without major surgery. The procedure is performed using an access point in a femoral vein 601 in the groin of the patient 600 using tools and techniques commonly used in interventional cardiology and radiology. One end of the catheter can be left outside of the body for the test period that requires only a short duration. Later, if the atrial stretching therapy is clinically successful, an implanted pump or a simple implanted subcutaneous infusion port such as a commercially available Port-A-Cath™ device can be connected to the already implanted catheter for repeat infusions and withdrawals of fluid into and from the balloon 505. Alternatively the balloon can be inserted into the RAA surgically by piercing the wall of the RAA 508 from the outside. The actual method of inserting and securing the balloon in the RAA will not change the substance of the invention. General approach in implantable devices is that less invasive methods of implantation are preferred in most cases but tend to be more demanding.

In the illustrated embodiment the pump 602 in implanted in a pocket under the patient's skin. All the mechanisms of the pump are enclosed in a titanium or polymer case. Fluid is stored in the internal reservoir (not shown). To refill the pump or to add or remove fluid, a needle 602 can be used to puncture the patient's skin and the pump reservoir septum (Not shown). The catheter 504 is in bidirectional fluid communication with the pump 602 and the balloon 505. All the fundamental elements described above are known to the developers of implantable drug pumps. An example of an implantable drug infusion device is the MiniMed 6007™ implantable insulin pump system for treatment of diabetes or the SynchroMed™ Infusion System used to control chronic pain, both manufactured by Medtronic Inc.

The proposed embodiment is different from the existing implantable drug infusion pumps in the following significant way. In existing drug infusion pumps fluid is infused in one direction always from the implanted pump reservoir into the body. In this invention the fluid is bidirectionally moved (shuttled) inside a closed system in both directions between the implanted pump and the implanted balloon. Historically implantable infusion devices have been used for intravenous, intraarterial, intrathecal, intraperitoneal, intraspinal and epidural drug delivery but not to control inflation and deflation of implanted balloons.

For the purpose of an estimate the balloon 105 can have a diameter of 1 cm when the RAA is not stretched and the diameter of 2 to 3 cm when the RAA is stretched. The balloon is 3 cm long. This implies shuttling of approximately 5 to 20 ml of incompressible fluid between the pump reservoir and the balloon. This requirement is within reasonable range for a fully implanted pump of the described type. The Medtronic SynchroMed pump for example has a miniature peristaltic pump mechanism that can be modified to operate bidirectionally and generate necessary pressures. It also has an internal fluid reservoir of 30 ml. The fluid can be a sterile, biocompatible fluid that will not harm the patient if it leaks out such as saline, glycerin or medical grade oil. The balloon 105 can be made of silicone, nylon or other strong medical plastic suited for multiple cycle inflation and deflation. Methods and materials for manufacturing of durable, implantable balloons exist and have been successfully implemented in many medical device applications.

The therapy may include the following steps:

Identifying a patient that will benefit from elevated levels of ANP and BNP likely from the group with heart failure, fluid retention or hypertension Implanting an expandable device in an atrial appendage of the patients heart Periodically expanding and contracting the device to temporarily stretch the walls of the atrium to achieve therapeutically significant increase of blood hormones.

The exact regiment of stretching and contracting the atrial wall is likely to be individual for each patient. For example a regiment can be proposed where the balloon is inflated for several minutes followed by several minutes of rest. These cycles will be repeated for several hours several times each day. In heart failure patients with fluid retention the objective of therapy will be to achieve minimum additional urine output of 250 ml per day and preferably 500 ml per day. The high end of the therapeutic range may be 1,000 additional ml of urine per day. This additional urine output is likely to improve patient's condition, allow more exercise and prevent hospital admissions from fluid overload. It is likely that the device will require a pump component that is remotely programmable so that the therapy parameters can be adjusted using wireless communication.

The adjustable programmable parameters may include:

Volume of Balloon Expansion

Duty cycle and frequency of inflation cycles in each therapy session

Number and time of therapy sessions hourly, daily or weekly

The methodology of programming an implantable pump is not different from programming a common heart pacemaker.

The invention has been described in connection with the best mode now known to the applicant inventors. The invention is not to be limited to the disclosed embodiment. Rather, the invention covers all of various modifications and equivalent arrangements included within the spirit and scope of the appended claims.

What is claimed is:

1. A method for pacing a heart of a patient suffering from at least one of hypertension, and excessive retention of fluid and sodium, the method comprising:

during a first pacing period synchronously pacing at least one atria and at least one ventricle of the patient's heart;

during a second pacing period,
synchronously pacing the at least one ventricle of the patient's heart at a ventricular pacing rate, and
producing extra contractions of the at least one atria by asynchronously pacing the at least one atria of the patient's heart at an atrial pacing rate that exceeds the ventricular pacing rate,
wherein the produced extra contractions stress a wall of the at least one atria beyond a natural stress condition, such that the stressed wall secretes a hormone at an elevated secretion level above a secretion level occurring while a natural atrial rate and a natural ventricular rate are equal; and achieving a beneficial therapeutic effect in the patient by the elevated level of the secreted hormone, wherein the beneficial therapeutic effect includes at least one of: limiting a degree of vasoconstriction, limiting a degree of sodium retention, increasing urine output, inhibiting a renin-angiotensin system, inhibiting endothelin secretion, inhibiting systemic and renal sympathetic activity, and counteracting effects of at least one of norepinephrine, endothelin, and angiotensin II.

2. The method of claim 1, further including blocking electric conduction from the atrium to the ventricle of the patient's heart during the second pacing period.

3. The method of claim 1, further including sensing a sinus rhythm of the patient's heart and selectively synchronizing the ventricular pacing rate with the sinus rhythm.

4. The method of claim 1, wherein the first pacing period is of a longer duration than the second pacing period.

5. The method of claim 1, wherein the secreted hormone is at least one of an atrial natriuretic peptide (ANP) and a brain natriuretic peptide (BNP).

6. The method of claim 1, wherein the beneficial therapeutic effect includes a treatment of heart failure.

7. The method of claim 1, wherein the pacing during the first pacing period is artificially induced by a pacing device.

8. The method of claim 1, further comprising repeatedly alternating the first pacing period and the second pacing period to pace the patient's heart.

9. The method of claim 1, wherein each alternating second pacing period has a duration of at least ten minutes.

10. A method for treating a patient suffering from at least one of hypertension, and excessive retention of fluid and sodium, the method comprising:

during a first pacing period synchronously pacing at least one atria and at least one ventricle of a heart of the patient;

during a second pacing period,
pacing the patient's heart to cyclically contract the at least one atria, stress a wall of the at least one atria, and restore the wall of the at least one atria to a substantially pre-stressed condition;
such that the stressed wall secretes a hormone at an elevated level above a natural secretion level occurring naturally when the patient's heart is not paced; and achieving a beneficial therapeutic effect in the patient by the hormone secreted at the elevated level, wherein the beneficial therapeutic effect includes at least one of: limiting a degree of vasoconstriction, limiting a degree of sodium retention, increasing urine output, inhibiting a renin-angiotensin system, inhibiting endothelin secretion, inhibiting systemic and renal sympathetic activity, and counteracting effects of at least one of norepinephrine, endothelin, and angiotensin II.

11. The method of claim 10, wherein pacing the patient's heart during the second pacing period comprises pacing the at least one ventricle at a ventricular pacing rate and pacing the at least one atria of the patient's heart at an atrial pacing rate that exceeds the ventricular pacing rate.

12. The method of claim 10, wherein pacing the patient's heart during the second pacing period to cyclically stress the wall of the at least one atria comprises pacing the at least one atria at an accelerated rate that causes extra contractions of the at least one atria.

13. The method of claim 10, wherein pacing the patient's heart during the second pacing period to cyclically stress the wall of the at least one atria comprises pacing an atrium of the patient's heart to contract atrial muscle at a cyclical rate faster than a ventricular contraction rate of the patient's heart.

14. The method of claim 10, wherein the pacing during the first pacing period is artificially induced by a pacing device.

15. The method of claim 10, further comprising repeatedly alternating the first pacing period and the second pacing period to pace the patient's heart.

16. The method of claim 15, wherein each alternating second pacing period has a duration of at least ten minutes.

17. A method for treating a patient suffering from at least one of hypertension, and excessive retention of fluid and sodium, the method comprising:

during a first pacing period synchronously pacing at least one atria and at least one ventricle of a heart of the patient;

during a second pacing period,
producing extra contractions of the at least one atria by pacing the at least one atria at an atrial contraction rate faster than a ventricular contraction rate,
wherein the produced extra contractions stress at least one wall of the at least one atria of the patient's heart so as to induce a tissue in the at least one stressed wall to secrete greater amounts of a hormone as compared to a secretion amount of the hormone occurring when no pacing is applied to the patient's heart; and achieving a beneficial therapeutic effect to the patient due to the secretion of the greater amounts of the hormone, wherein the beneficial therapeutic effect includes at least one of: limiting a degree of vasoconstriction, limiting a degree of sodium retention, increasing urine output, inhibiting a renin-angiotensin system, inhibiting endothelin secretion, inhibiting systemic and renal sympathetic activity, and counteracting effects of at least one of: norepinephrine, endothelin, and angiotensin II.

18. The method of claim 17, wherein producing the extra contractions of the at least one atria during the second pacing period comprises pacing an atrium at an atrial pacing rate that is faster than the ventricular contraction rate.

19. The method of claim 17, wherein the second pacing period comprises pacing a ventricle of the patient's heart at a ventricular pacing rate slower than the atrial contraction rate.

20. The method of claim 17, further comprising atrioventricular blocking of atrial electric impulses from reaching a ventricle of the patient's heart during the second pacing period.

21. The method of claim 17, further comprising atrioventricular blocking of atrial depolarization from reaching a ventricle of the patient's heart and causing ventricular depolarization during the second pacing period.

22. The method of claim 17, wherein the pacing during the first pacing period is artificially induced by a pacing device.

23. The method of claim 17, further comprising repeatedly alternating the first pacing period and the second pacing period to pace the patient's heart.

24. The method of claim 17, wherein each alternating second pacing period has a duration of at least ten minutes.

\* \* \* \* \*